(12) United States Patent
Pasanen et al.

(10) Patent No.: US 8,608,966 B2
(45) Date of Patent: Dec. 17, 2013

(54) METHOD AND APPARATUS FOR DEWATERING A MIXTURE OF ETHANOL AND WATER

(75) Inventors: Antti Pasanen, Espoo (FI); Mikko Ahokas, Helsinki (FI)

(73) Assignee: ST1 Biofuels Oy, Helsinki (FI)

( * ) Notice: Subject to any disclaimer, the term of this patent is extended or adjusted under 35 U.S.C. 154(b) by 317 days.

(21) Appl. No.: 12/921,114

(22) PCT Filed: Nov. 7, 2008

(86) PCT No.: PCT/FI2008/050638
§ 371 (c)(1),
(2), (4) Date: Mar. 4, 2011

(87) PCT Pub. No.: WO2009/109686
PCT Pub. Date: Sep. 11, 2009

(65) Prior Publication Data
US 2011/0152584 A1    Jun. 23, 2011

(30) Foreign Application Priority Data
Mar. 5, 2008    (FI) .................................... 20085209

(51) Int. Cl.
*B01D 15/00* (2006.01)
*B01D 53/22* (2006.01)
*B01D 35/18* (2006.01)
*C02F 1/02* (2006.01)

(52) U.S. Cl.
USPC .............. 210/640; 210/175; 210/180; 95/52; 203/10; 203/11; 203/12; 203/14; 202/82; 202/180

(58) Field of Classification Search
USPC ................ 210/640, 175, 180; 203/10–12, 14; 95/52; 202/82, 180
See application file for complete search history.

(56) References Cited

U.S. PATENT DOCUMENTS

| 4,911,845 A | 3/1990 | Hashimoto et al. |
| 5,105,029 A | 4/1992 | Ninomiya et al. |

(Continued)

FOREIGN PATENT DOCUMENTS

| EP | 0701 857 A1 | 3/1996 |
| JP | 58 021629 A | 2/1983 |

(Continued)

OTHER PUBLICATIONS

Supplementary European Search Report, PCT/FI2008/050638, dated Jun. 22, 2012.

(Continued)

*Primary Examiner* — Ana Fortuna
(74) *Attorney, Agent, or Firm* — Hamilton, Brook, Smith & Reynolds, P.C.

(57) ABSTRACT

The invention relates to a method and an apparatus for dewatering mixture of ethanol and water. The method comprises steps for feeding mixture of ethanol and water (1) into an evaporator (2), evaporating said mixture of ethanol and water (1) and feeding a stream of vaporized mixture of ethanol and water (3) to a vapor recompression unit (4), pressurizing vaporized mixture of ethanol and water (3) in the vapor recompression unit (4) and feeding a stream of pressurized vaporized mixture of ethanol and water (5) to a membrane unit (6), and dividing said stream of pressurized mixture of ethanol and water (5) in to a stream of mixture of ethanol and water (8) and into a stream of dewatered mixture of ethanol and water (7).

14 Claims, 3 Drawing Sheets

(56) References Cited

U.S. PATENT DOCUMENTS

Figure 1:
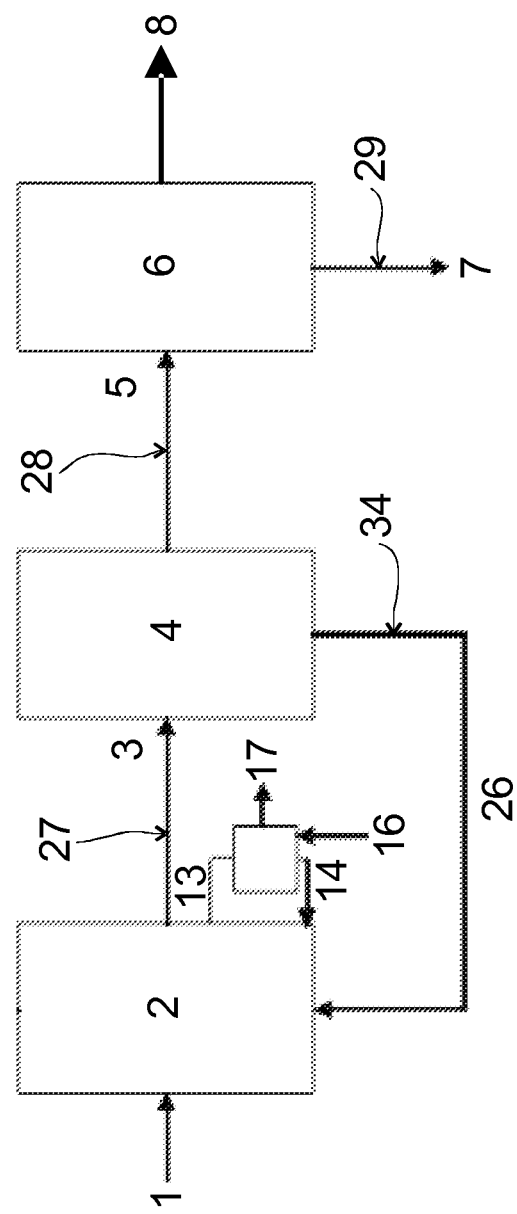

| | | | |
|---|---|---|---|
| 5,143,526 A * | 9/1992 | Lee et al. ................... 210/195.2 |
| 5,681,433 A | 10/1997 | Friesen et al. |
| 7,594,981 B2 * | 9/2009 | Ikeda ............................... 203/18 |
| 2006/0070867 A1 * | 4/2006 | Ikeda ............................... 203/25 |
| 2007/0031954 A1 | 2/2007 | Mairal et al. |
| 2008/0207959 A1 * | 8/2008 | Plante et al. .................. 568/916 |
| 2009/0246848 A1 * | 10/2009 | Noel ............................. 435/165 |

FOREIGN PATENT DOCUMENTS

| | | | |
|---|---|---|---|
| JP | 63059308 A | 3/1988 |
| JP | 63254987 A | 10/1988 |
| JP | 63258601 A | 10/1988 |
| JP | 5137970 A | 6/1993 |
| WO | WO 2009/048335 A1 | 4/2009 |

OTHER PUBLICATIONS

International Search Report, International Application No. PCT/IF2008/050638, date of mailing Feb. 26, 2009.

International Preliminary Report on Patentability, International Application No. PCT/FI2008/050638, date of completion of report, Jun. 14, 2010.

Finnish Search Report, Application No. 20085209, dated Aug. 26, 2008.

* cited by examiner

US 8,608,966 B2

METHOD AND APPARATUS FOR DEWATERING A MIXTURE OF ETHANOL AND WATER

This application is the U.S. National Stage of International Application No. PCT/FI2008/050638, filed Nov. 7, 2008, which designates the U.S., published in English, and claims priority under 35 U.S.C. §119 or 365(c) to Finland Application No. 20085209, filed Mar. 5, 2008.

FIELD OF THE INVENTION

The invention relates to a method for dewatering mixture of ethanol and water.

The invention also relates to an apparatus for dewatering mixture of ethanol and water.

The invention also relates to the use of the method and apparatus for concentration of a mixture of ethanol and water.

The invention relates to distillation or dewatering or dehydration of mixture of ethanol and water preferably, but not necessarily, from a ethanol content by volume of about 80 to about 96% to a ethanol content by volume of about 99.7 to about 99.8%, which is suitable to be used as a component in fuel containing for example 85% ethanol and 15% gasoline (e85) or to be used as fuel-grade ethanol.

Publication U.S. Pat. No. 4,911,845 discloses a process for the mutual separation of volatile components in a mixture comprising at least two volatile components. The process comprising the steps of: (1) heating a starting liquid comprising at least two volatile components to vaporize the starting liquid and form a vapor mixture comprising the volatile component, (2) compressing the vapor mixture to cause a rise in the temperature and pressure thereof, (3) applying the compressed vapor mixture to a membrane having a selective permeability to separate the vapor mixture into a membrane-permeated fraction and a non membrane-permeated fraction, (4) indirectly placing at least one of the fractions in contact with the starting liquid of step (1) via a heat transferring wall to use the heat of the contacted fraction to vaporize the starting liquid, and (5) recovering one or both of the membrane-permeated fraction and non membrane-permeated fraction. This publication U.S. Pat. No. 4,911,845 discloses also an apparatus for a mutual separation of volatile components in a mixture comprising at least two volatile components, comprising: (1) an evaporator having at least one heat exchanger into which at least one fraction separated by a membrane separator of (3) is introduced, a starting liquid feeding side, an evaporation residue discharging side, and an optional auxiliary heater; to generate a vapor mixture, (2) a compressor to compress the vapor mixture, and (3) a membrane separator comprising a member having a selective permeability to separate the compressed vapor mixture into a membrane-permeated faction and a non membrane-permeated fraction.

OBJECTIVE OF THE INVENTION

The object of the invention is to provide an energy efficient novel and inventive method and apparatus for dewatering mixture of ethanol and water.

SHORT DESCRIPTION OF THE INVENTION

In the method of the invention mixture of ethanol and water is fed into an evaporator. In the evaporator said mixture of ethanol and water is evaporated. A stream of vaporized mixture of ethanol and water is fed from the evaporator to a vapor recompression unit. In the vapor recompression unit the vaporized mixture of ethanol and water is pressurized to raise the pressure and the temperature of the vaporized mixture of ethanol and water. A stream of pressurized vaporized mixture of ethanol and water is fed from the vapor recompression unit to a membrane unit. In the membrane unit said stream of pressurized vaporized mixture of ethanol and water is divided into a stream of mixture of ethanol and water and into a stream of dewatered mixture of ethanol and water. A stream of vaporized mixture of ethanol and water is fed from the membrane unit. A stream of dewatered mixture of ethanol and water is fed from the membrane unit.

Effective separation of said stream of pressurized vaporized mixture of ethanol and water in the membrane unit into a stream of vaporized mixture of ethanol and water and into a stream of dewatered mixture of ethanol and water requires that the temperature and the pressure of the feed is high. If the pressure and/or the temperature of the feed are too low, there is a risk that the vapor feed condense on the membranes in the membrane unit and prevents permeation through the membranes. By using a vapor recompressing unit in combination with the evaporator, which vapor recompressing unit is placed downstream of the evaporator for recompressing the vaporized mixture of ethanol and water evaporated in the evaporation unit, both the temperature and the pressure of the feed can be raised in an energy-effective way in comparison to a method/arrangement in which the mixture of ethanol and water evaporated is evaporated and heated to the desired temperature in one-step in an evaporator. A such method/arrangement in which the mixture of ethanol and water evaporated is evaporated and heated to the desired temperature in one-step in an evaporator needs about 2.5 times more energy for raising (vaporizing) the temperature of a mixture of ethanol and water from 20° C. to over 135° C., preferably to over 150° C., more preferable to over 170° C. than a apparatus having a recompression unit in combination with an evaporator.

In a preferable embodiment of the invention said stream of pressurized mixture of ethanol and water is divided in the membrane unit in a vapor permeation step into a vaporized permeate stream of vaporized mixture of ethanol and water and into a retentate stream of dewatered mixture of ethanol and water. In this preferable embodiment of the invention a vaporized permeate stream of vaporized mixture of ethanol and water is fed from the membrane unit. In this preferable embodiment of the invention a retentate stream of dewatered mixture of ethanol and water is fed from the membrane unit.

In a preferred embodiment of the invention said stream of pressurized mixture of ethanol and water is divided in the membrane unit in a vapor permeation step into a vaporized permeate stream of vaporized mixture of ethanol and water and into a retentate stream of dewatered mixture of ethanol and water. In this preferable embodiment of the invention the retentate stream of dewatered mixture of ethanol and water is fed i.e. discharged from the membrane unit. In this preferable embodiment of the invention the vaporized permeate stream of vaporized mixture of ethanol and water is fed from the membrane unit to a dewatering means for dividing the vaporized permeate stream of vaporized mixture of ethanol and water into a stream of dewatered mixture of ethanol and water and into a stream of water. In this preferred embodiment of the invention, the stream of water is discharged from the dewatering means and the stream of dewatered mixture of ethanol and water is fed back into the evaporator. An advantage with this preferred embodiment in which a vaporized permeate stream of vaporized mixture of ethanol and water is fed from the membrane unit for further processing in a dewatering unit is that it provides for separating of water from the vaporized permeate stream of vaporized mixture of ethanol and water. Water separated from the vaporized permeate stream of vaporized mixture of ethanol and water can be removed from the process and because this water is essentially free from ethanol (contains for example less than 0.2% ethanol) the processing of this water is normally not difficult. Because of the low ethanol content, the water can for example be fed into the sewer system for possible further processing in a sewage treatment facility. Another advantage with this preferred embodiment in which a vaporized permeate stream of vaporized mixture of ethanol and water is fed from the membrane unit for further processing in a dewatering unit is that it provides for dewatering i.e. concentrating of the vaporized permeate stream of vaporized mixture of ethanol and water and for reusing of the dewatered i.e. concentrated mixture of ethanol and water in the evaporator by feeding the concentrated mixture of ethanol and water from the distilling unit to the evaporator.

In another preferred embodiment of the invention said stream of pressurized mixture of ethanol and water is divided in the membrane unit in a vapor permeation step into a vaporized permeate stream of vaporized mixture of ethanol and water and into a retentate stream of dewatered mixture of ethanol and water. In this preferable embodiment of the invention a retentate stream of dewatered mixture of ethanol and water is fed from the membrane unit. In this preferable embodiment of the invention the vaporized permeate stream of vaporized mixture of ethanol and water is fed from the membrane unit to a dewatering means for dividing the vaporized permeate stream of vaporized mixture of ethanol and water into a stream of dewatered mixture of ethanol and water and into a stream of water. In this preferred embodiment the dewatering means comprises a cooling unit and a distilling unit. In this preferable embodiment of the invention the vaporized permeate stream of vaporized mixture of ethanol and water is fed from the membrane unit to said cooling unit and the vaporized permeate stream of vaporized mixture of ethanol and water is condensed in the cooling unit to a liquid permeate vaporized mixture of ethanol and water. In this preferable embodiment of the invention a liquid permeate stream of vaporized mixture of ethanol and water is fed from the cooling unit into said distilling unit. In this preferable embodiment of the invention the liquid permeate stream of vaporized mixture of ethanol and water is divided in the distilling unit in a distillation step into a stream of vaporized mixture of ethanol and water and into a stream of water. In the preferable embodiment of the invention the stream of vaporized mixture of ethanol and water from the distilling unit back to the evaporator. An advantage with this preferred embodiment in which a vaporized permeate stream of vaporized mixture of ethanol and water is fed from the membrane unit for further processing is that it provides for further or additional separating of water from the vaporized permeate stream of vaporized mixture of ethanol and water. Water separated from the vaporized permeate stream of vaporized mixture of ethanol and water can be removed from the process and because this water is essentially free from ethanol (contains for example less than 0.2% ethanol) the processing of this water is normally not difficult. Because of the low ethanol content, the water can for example be fed into the sewer system for possible further processing in a sewage treatment facility. Another advantage with this preferred embodiment in which a vaporized permeate stream of vaporized mixture of ethanol and water is fed from the membrane unit for further processing is that it provides for dewatering i.e. concentrating of the vaporized permeate stream of vaporized mixture of ethanol and water and for reusing of the dewatered i.e. concentrated mixture of ethanol and water in the evaporator by feeding the concentrated mixture of ethanol and water from the distilling unit to the evaporator.

In a preferred embodiment of the invention a membrane comprising a membrane comprising a Zeolite material such as Zeolite NaA is preferably used in the membrane unit. Separation of water and ethanol in a Zeolite membrane is based on differences in adsorption and diffusion rates of the water and ethanol molecules through the Zeolite membrane. An advantage of Zeolite membranes is their relatively high maximum operating temperature, which means that the temperature and the pressure of the vapor feed can be high in comparison to e.g. polymer membranes. In other words in this preferred embodiment the temperature of the pressurized vaporized mixture of ethanol and water fed from the vapor recompression unit to the membrane unit comprising a membrane comprising a Zeolite material such as Zeolite NaA can be high. This provides for an effective separation of ethanol from the pressurized vaporized mixture of ethanol and water in the membrane unit.

In a preferred embodiment of the invention the temperature of the vaporized mixture of ethanol and water is raised in the vapor recompression unit to over 135° C., preferably to over 150° C., more preferably to about 170° C. prior filing of the vaporized mixture of ethanol and water into the membrane unit. A temperature of over 140° C., preferably to over 150° C., more preferably to about 170° C., provides for an effective separation of ethanol from water in the membrane unit, because the high temperature of the pressurized vaporized mixture of ethanol and water creates a high pressure difference between the sides of the membranes in the membrane unit, e.g. retentate side 5.5 bar and permeate side 100 mbar, which provided for effective penetration of water molecules through the membrane, in other words for effective separation of ethanol from water.

In a preferred embodiment of the invention the temperature of the vaporized mixture of ethanol and water is raised in the vapor recompression unit to over 140° C., preferably to over 150° C., more preferably to about 170° C. prior filing of the vaporized mixture of ethanol and water into the membrane unit comprising a membrane comprising a Zeolite material i.e. a Zeolite membrane. A temperature of over 140° C., preferably to over 150° C., more preferably to about 170° C., provides for an effective separation of ethanol from water in the Zeolite membrane in the membrane unit, because the high temperature of the pressurized vaporized mixture of ethanol and water creates a high pressure difference between the sides of the Zeolite membrane in the membrane unit, which provided for effective penetration of water molecules through the membrane, in other words for effective separation of ethanol from water.

LIST OF FIGURES

Figure 2:
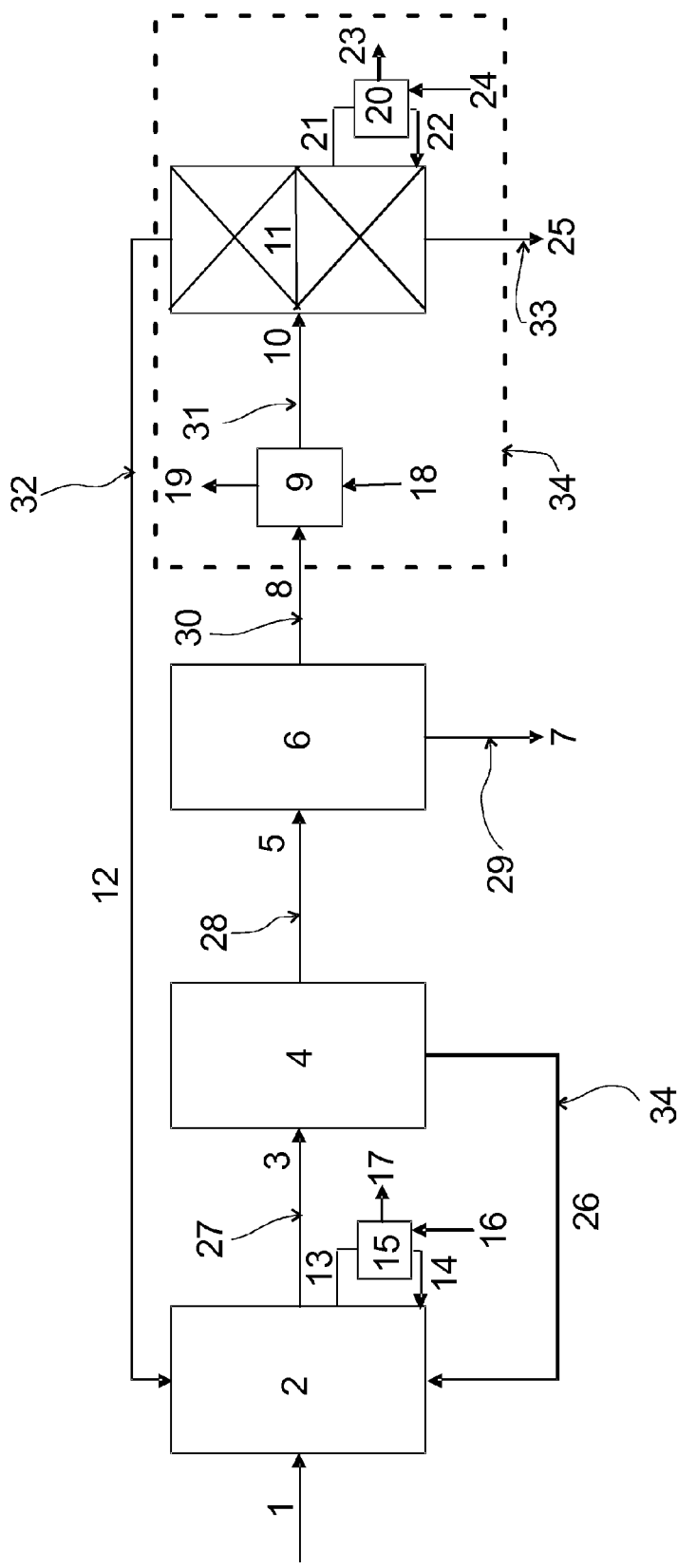
Figure 3:
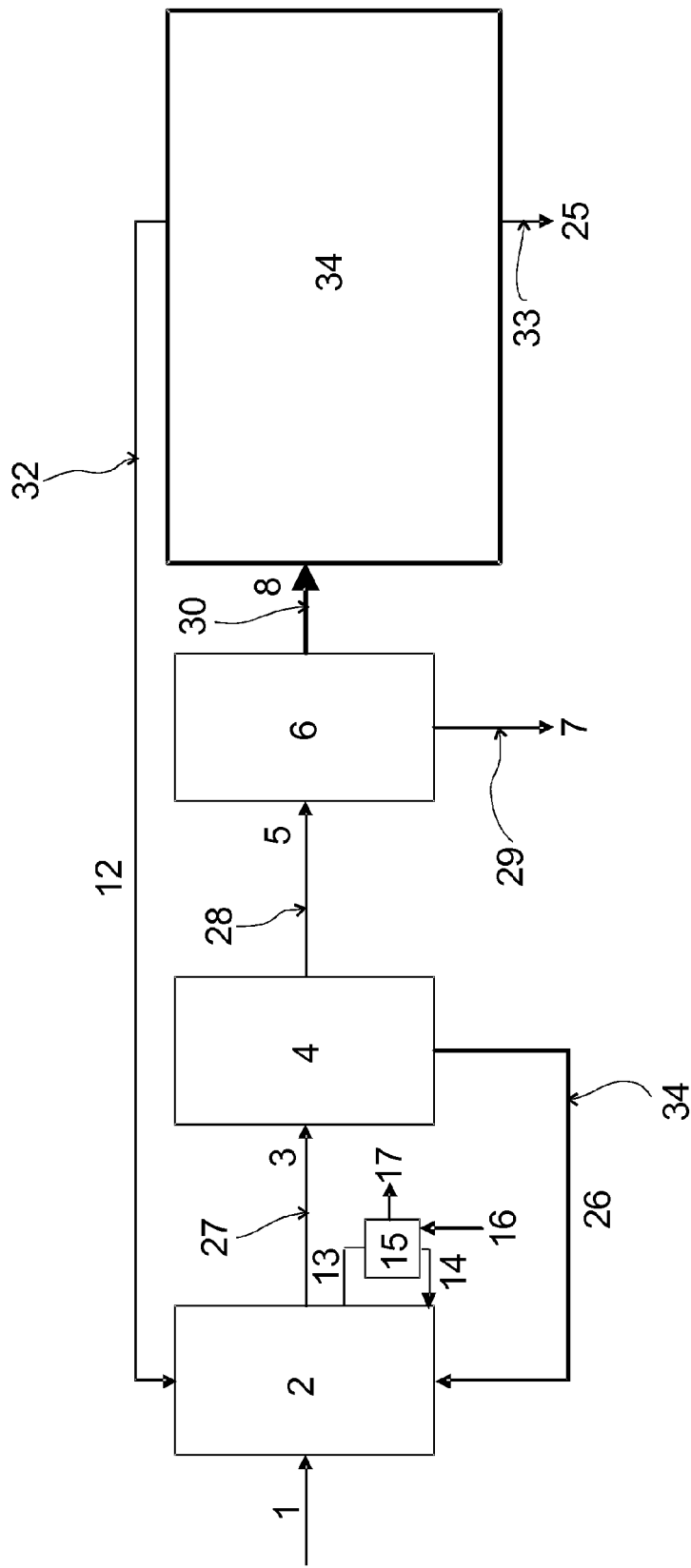

In the following the invention will described in more detail by referring to the figures of which FIG. 1 shows a flow sheet of a first preferred embodiment of the invention, FIG. 2 shows a flow sheet of a second preferred embodiment of the invention, and FIG. 3 shows a flow sheet of a third preferred embodiment of the invention.

DETAILED DESCRIPTION OF THE INVENTION

The figures show examples of a method and an apparatus according to the invention.

The apparatus shown in FIGS. 1 to 3 comprises an evaporator 2 for receiving mixture of ethanol and water 1 and for evaporating mixture of ethanol and water 1. The mixture of ethanol and water 1 contains preferably, but not necessarily, an ethanol content by volume of about 80%, In the figures the evaporator comprises a boiler 15 for heating and vaporizing mixture of ethanol and water and circulation means 13 and 14 for circulating vaporized mixture of ethanol and water through the boiler 15. In the figures the boiler 15 comprises heat exchanging means (not shown in the figures) for transferring thermal energy from a fluid 16 and 17 circulating via the heat exchanging means of the boiler 15 to the mixture of ethanol and water circulating through the boiler 15 for heating the mixture of ethanol and water. 1

The apparatus shown in FIGS. 1 to 3 comprises also first conduit means 27 for feeding a stream of vaporized mixture of ethanol and water 3 from the evaporator 2 to a vapor recompression unit 4 for pressurizing and raising the temperature of said vaporized mixture of ethanol and water 3.

The apparatus shown in FIGS. 1 to 3 comprises also second conduit means 28 for feeding a stream of pressurized vaporized mixture of ethanol and water 5 from the vapor recompression unit 4 to a membrane unit 6 for dividing said stream of pressurized mixture of ethanol and water 5 into a stream of mixture of ethanol and water 8 and into a stream of dewatered mixture of ethanol and water 7 i.e. a stream of mixture of ethanol and water 7 containing less water than said stream of pressurized vaporized mixture of ethanol and water 5.

The apparatus is preferably, but not necessarily, configured for continuously feeding a stream of pressurized vaporized mixture of ethanol and water 5 from the vapor recompression unit 4 to the membrane unit 6.

The membrane unit 6 for dividing said stream of pressurized mixture of ethanol and water 5 is preferably, but not necessarily, configured to divide said stream of pressurized mixture of ethanol and water 5, pressure e.g. 5.5 bar, in a vapor permeation step into a vaporized permeate stream of vaporized mixture of ethanol and water 8, pressure e.g. 100 mbar, and into a retentate stream of dewatered mixture of ethanol and water vapour 7.

The membrane unit 6 comprises preferably, but not necessarily, at least one of the following: a semipermeable membrane, a porous membrane, a ceramic membrane, a molecular sieve, a membrane comprising a Zeolite material such as Zeolite NaA, and a Zeolite membrane.

The vapor recompression unit 4 comprises preferably, but not necessarily, at least one of the following: a mechanical vapor recompression unit and thermal vapor recompression unit.

The apparatus shown in FIGS. 1 to 3 comprises third conduit means 29 feeding the stream of dewatered mixture of ethanol and water 7 from the membrane unit 6. This stream of dewatered mixture of ethanol and water 7 contains preferably, but not necessarily, an ethanol content by volume of about 99.7 to about 99.8%, If the membrane unit 6 for dividing said stream of pressurized mixture of ethanol and water 5 is configured to divide said stream of pressurized mixture of ethanol and water 5 in a vapor permeation step into a vaporized permeate stream of vaporized mixture of ethanol and water 8 and into a retentate stream of dewatered mixture of ethanol and water 7, the third conduit means 29 is configured for feeding a retentate stream of dewatered mixture of ethanol and water 7 from the membrane unit 6.

The apparatus comprises in a preferred embodiment fourth conduit means 30 for feeding the vaporized permeate stream of vaporized mixture of ethanol and water 8 from the membrane unit 6 to a dewatering means 34 for dividing the vaporized permeate stream of vaporized mixture of ethanol and water 8 into a stream of dewatered mixture of ethanol and water 12 and into a stream of water 25. In this embodiment, the apparatus comprises also sixth conduit means 32 for feeding the stream of dewatered mixture of ethanol and water 12 from the dewatered unit 34 to the evaporator 2 and seventh conduit means 33 for discharging the stream of water 25 from the dewatering unit 34.

The apparatus shown in FIG. 3 comprises fourth conduit means 30 for feeding the vaporized permeate stream of vaporized mixture of ethanol and water 8 from the membrane unit 6 to a dewatering means 34 for dividing the vaporized permeate stream of vaporized mixture of ethanol and water 8 into a stream of vaporized dewatered mixture of ethanol and water 12 and into a stream of water 25.

The apparatus shown in FIG. 3 comprises also sixth conduit means 32 for feeding the stream of vaporized dewatered mixture of ethanol and water 12 from the dewatering unit 34 to the evaporator 2

The apparatus shown in FIG. 3 comprises also seventh conduit means 33 for discharging the stream of water 25 from the dewatering unit 34.

In the apparatus shown in FIG. 2 the dewatering unit 34 comprises a cooling unit 9 and a distilling unit 11.

The apparatus shown in FIG. 2 comprises fourth conduit means 30 for feeding a vaporized permeate stream of vaporized mixture of ethanol and water 8 from the membrane unit 6 to the cooling unit 9 for condensing the vaporized permeate stream of vaporized mixture of ethanol and water 8 to a liquid permeate vaporized mixture of ethanol and water 10.

In FIG. 2 the cooling unit 9 is provided with a circulation system for circulating a cooling fluid 18 and 19 through the cooling unit. As said cooling fluid 18 and 19 may a fluid flow in the apparatus having a lower temperature than said vaporized permeate stream of vaporized mixture of ethanol and water 8 be used.

The apparatus shown in FIG. 2 comprises fifth conduit means 31 feeding a liquid permeate stream of vaporized mixture of ethanol and water 10 from the cooling unit 9 into the distilling unit 11 for dividing the liquid permeate stream of vaporized mixture of ethanol and water 8 in a distillation step into a stream of vaporized mixture of ethanol and water 12 and into a stream of water 25. The distilling unit 11 preferably, but not necessarily, comprises a distillation column.

In FIG. 2 the distilling unit 11 is provided with a reboiler 20 for providing heat to the distilling unit 11 by boiling bottoms liquid 21 and 22 of the distilling unit 11. The reboiler is provided with a heat exchanger through which bottoms liquid 21 and 22 and heating fluid 23 and 24 can be circulated so that thermal energy of the heating fluid 23 and 24 can heat the bottoms liquid 21 and 22.

The apparatus shown in FIG. 2 comprises sixth conduit means 32 for feeding the stream of vaporized mixture of ethanol and water 12 from the distilling unit 11 to the evaporator 2.

The apparatus shown in FIG. 2 comprises seventh conduit means 33 for feeding the water 25 from the distilling unit 11.

The apparatus shown in FIGS. 1 to 3 comprises eight conduit means 34 for feeding steam 26 from the vapor recompression unit 34 to the evaporator.

The apparatus shown in FIGS. 1 to 3 comprises also preferably, but not necessarily, at least one flow means such as a pump for example a vacuum pump and/or a compressor for example a vacuum compressor for creating required flows through the various devices of the apparatus.

Then invention also relates to a method for dewatering mixture of ethanol and water.

The method comprises a step for feeding mixture of ethanol and water 1 into an evaporator 2. The mixture of ethanol and water 1 contains preferably, but not necessarily, an ethanol content by volume of about 80%, The method comprises a step for evaporating said mixture of ethanol and water 1 in the evaporator 2 and feeding a stream of vaporized mixture of ethanol and water 3 from the evaporator 2 to a vapor recompression unit 4.

The method comprises a step for pressurizing and raising the temperature of vaporized mixture of ethanol and water 3 in the vapor recompression unit 4 and feeding a stream of pressurized vaporized mixture of ethanol and water 5 from the vapor recompression unit 4 to a membrane unit 6. The method comprises more preferably a step for pressurizing and raising the temperature of vaporized mixture of ethanol and water 3 in the vapor recompression unit 4 and for continuously feeding a stream of pressurized vaporized mixture of ethanol and water 5 from the vapor recompression unit 4 to a membrane unit 6. The temperature of vaporized mixture of ethanol and water 3 is preferably, but not necessarily, raised to over 150° C., preferably to about 170° C. A high temperature provided for an effective separation of ethanol from water.

The method comprises a step for dividing said stream of pressurized mixture of ethanol and water 5 in the membrane unit 6 into a stream of mixture of ethanol and water 8 and feeding the stream of mixture of ethanol and water 8 from the membrane unit 6 and into a stream of dewatered mixture of ethanol and water 7 and feeding the stream of dewatered mixture of ethanol and water 7 from the membrane unit 6. This step of the method in preferably, but not necessarily, in the form of a step for dividing said stream of pressurized mixture of ethanol and water 5 in the membrane unit 6 in a vapor permeation step into a vaporized permeate stream of vaporized mixture of ethanol and water 8 and feeding the a vaporized permeate stream of vaporized mixture of ethanol and water 8 from the membrane unit 6 and into a retentate stream of dewatered mixture of ethanol and water 7 and feeding the retentate stream of dewatered mixture of ethanol and water 7 from the membrane unit 6. This stream of dewatered mixture of ethanol and water 7 contains preferably, but not necessarily, an ethanol content by volume of about 99.7 to about 99.8%, In the method is preferably, but not necessarily, at least one of the following used in the membrane unit 6: semipermeable membrane, a porous membrane, a ceramic membrane, a membrane comprising a molecular sieve, a membrane comprising a Zeolite material, and a Zeolite membrane. Especially if the temperature of vaporized mixture of ethanol and water 3 is raised in the vapor recompression unit to over 150° C., preferably to about 170° C., a membrane comprising a Zeolite material is preferably used in the membrane unit 6 due to the ability of Zeolite to withstand heat.

In the method is preferably, but not necessarily, at least one of the following used in the vapor recompression unit: a mechanical vapor recompression unit and thermal vapor recompression unit.

In a preferred embodiment of the method the vaporized permeate stream of vaporized mixture of ethanol and water 8 is fed from the membrane unit 6 into a dewatering means 34 for dividing the vaporized permeate stream of vaporized mixture of ethanol and water 8 into a stream of dewatered mixture of ethanol and water 12 and into a stream of water. In this preferred embodiment of the method shown the stream of water 25 is discharged from the dewatering means 34 and the stream of dewatered mixture of ethanol and water 12 is fed to the evaporator 2.

In the method shown in FIG. 3 the vaporized permeate stream of vaporized mixture of ethanol and water 8 is fed from the membrane unit 6 into a dewatering means 34 for dividing the vaporized permeate stream of vaporized mixture of ethanol and water 8 into a stream of vaporized dewatered mixture of ethanol and water 12 and into a stream of water.

In the method shown in FIG. 3 the stream of water 25 is discharged from the dewatering means 34 and the stream of vaporized dewatered mixture of ethanol and water 12 is fed to the evaporator 2.

In the method shown in FIG. 2 a dewatering means 34 comprising a cooling unit 9 and a distilling unit 11 is used.

In the method shown in FIG. 2 is the vaporized permeate stream of vaporized mixture of ethanol and water 8 fed from the membrane unit 6 to the cooling unit 9.

In the method shown in FIG. 2 is the vaporized permeate stream of vaporized mixture of ethanol and water 8 in the cooling unit 9 condensed to a liquid permeate vaporized mixture of ethanol and water 10 and a liquid permeate stream of vaporized mixture of ethanol and water 10 is fed into the distilling unit 11 that preferably, but not necessarily, comprises a distillation column.

In the method shown in FIG. 2 is the liquid permeate stream of vaporized mixture of ethanol and water 10 in the distilling unit 11 divided in a distillation step into a stream of vaporized mixture of ethanol and water 12 and into a stream of water 25.

In the method shown in FIG. 2 is bottoms liquid 21 and 22 of the distilling unit 11 circulated in a reboiler 20 heated by a liquid stream 23 and 24.

In the method shown in FIG. 2 is the stream of vaporized mixture of ethanol and water 12 fed from the distilling unit 11 to the evaporator 2.

In the method shown in FIG. 2 is water 25 fed from the distilling unit 11.

The method comprises also preferably, but not necessarily, a step of pressing and/or sucking at least one of the streams of the method through at least one of the devices used in the method by means of at least one flow means such as a pump for example a vacuum pump and/or a compressor for example a vacuum compressor for creating required flows through the various devices of the apparatus.

The method comprises also preferably, but not necessarily heat exchange by letting flow 7 to flow through a heat exchanger changing heat between flow 1 and flow 7, and/or by letting flow 7 to flow through the heat exchanger 15 and/or through the heat exchanger 20, in which heat exchangers the product ethanol vapor condensate, or partly condensate, into liquid and boils ethanol-water feed in vessel 2 and/or in vessel 11.

EXAMPLE

In the example an apparatus corresponding to the apparatus shown in FIG. 2 was used.

5140 kg 80% mixture of ethanol and water per hour was fed into an evaporator. 4440 kg 99.8% mixture of ethanol and water was obtained per hour from the membrane unit. In the example was 430 kW thermal energy used in the evaporator, 85 kW thermal energy used in the boiler of the distilling unit and 22 kW thermal energy was used as a barrier steam in the vapor recompression unit. In addition 75 kW electrical energy was used for driving a compressor of the vapor recompression unit. In other words the consumption of thermal energy was 537 kW for 5140 kg 80% mixture of ethanol and water (0.104 kW/kg) and the consumption of electrical energy was 75 kW for 5140 kg 80% mixture of ethanol and water (0.0146 kW/kg) which means that 0.1186 kW per kg 80% ethanol was used for dewatering 80% mixture of ethanol and water to 99.8% mixture of ethanol and water.

It is apparent to a person skilled in the art that as technology advanced, the basic idea of the invention can be implemented in various ways. The invention and its embodiments are therefore not restricted to the above examples, but they may vary within the scope of the claims.

LIST OF REFERENCE NUMERALS

1. Mixture of ethanol and water
2. Evaporator
3. Stream of vaporized mixture of ethanol and water
4. Vapor recompression unit
5. Stream of pressurized vaporized mixture of ethanol and water
6. Membrane unit
7. Stream of dewatered mixture of ethanol and water
8. Vaporized permeate stream of vaporized mixture of ethanol and water
9. Cooling unit
10. Liquid permeate stream of vaporized mixture of ethanol and water
11. Distilling unit
12. Stream of vaporized dewatered mixture of ethanol and water
13. Circulation means
14. Circulation means
15. Boiler
16. Fluid
17. Fluid
18. Cooling fluid
19. Cooling fluid
20. Reboiler
21. Bottoms liquid
22. Bottoms liquid
23. Heating fluid
24. Heating fluid
25. Stream of water
26. Steam
27. First conduit means
28. Second conduit means
29. Third conduit means
30. Fourth conduit means
31. Fifth conduit means
32. Sixth conduit means
33. Seventh conduit means
34. Eight conduit means
35. Dewatering means

The invention claimed is:

1. A method for dewatering a mixture of ethanol and water, comprising:
   feeding a mixture of ethanol and water into an evaporator,
   evaporating said mixture in the evaporator and feeding a stream of vaporized mixture of ethanol and water from the evaporator to a vapor recompression unit,
   pressurizing said vaporized mixture of ethanol and water in the vapor recompression unit and feeding a stream of pressurized vaporized mixture of ethanol and water from the vapor recompression unit to a membrane unit,
   dividing said stream of pressurized mixture of ethanol and water in the membrane unit in a vapor permeation step into (i) a vaporized permeate stream of vaporized mixture of residual ethanol and water and feeding the vaporized permeate stream of vaporized mixture of residual ethanol and water from the membrane unit and, (ii) into a retentate stream of dewatered mixture of ethanol and residual water from the membrane unit,
   using a dewatering unit comprising a cooling unit and a distillation column,
   feeding the vaporized permeate stream of vaporized mixture of residual ethanol and water from the membrane unit into the cooling unit of the dewatering unit and condensing the vaporized permeate stream of vaporized mixture of residual ethanol and water in the cooling unit to a liquid permeate stream of residual ethanol and water and feeding the liquid permeate stream of residual ethanol and water into the distillation column,
   dividing the liquid permeate stream of residual ethanol and water in the distillation column in a distillation step into (i) a second stream of dewatered mixture of ethanol and residual water, and into (ii) a stream of water,
   discharging the stream of water from the distillation column, and
   feeding the second stream of dewatered mixture of ethanol and residual water from the distillation column directly to the evaporator.

2. The method according to claim 1, further including using at least one of the following in the vapor recompression unit: a mechanical vapor recompression unit and a thermal vapor recompression unit.

3. The method according to claim 1, further including feeding continuously a stream of pressurized vaporized mixture of ethanol and water from the vapor recompression unit to the membrane unit.

4. The method according to claim 1, further including using a semipermeable membrane in the membrane unit.

5. The method according to claim 1, further including using a porous membrane in the membrane unit.

6. The method according to claim 1, further including using a ceramic membrane in the membrane unit.

7. The method according to claim 1, further including using a membrane comprising a Zeolite material in the membrane unit.

8. An apparatus for dewatering a mixture of ethanol and water, comprising:
   an evaporator for receiving a mixture of ethanol and water and for evaporating the mixture,
   first conduit for feeding a stream of vaporized mixture of ethanol and water from the evaporator to a vapor recompression unit for pressurizing said vaporized mixture of ethanol and water,
   second conduit for feeding a stream of pressurized mixture of ethanol and water from the vapor recompression unit to a membrane unit, wherein the membrane unit is configured to divide said stream of pressurized mixture of ethanol and water in a vapor permeation step into a vaporized permeate stream of vaporized mixture of residual ethanol and water and into a retentate stream of dewatered mixture of ethanol and residual water,
   a dewatering unit comprising a cooling unit and a distillation column,
   fourth conduit for feeding the vaporized permeate stream of vaporized mixture of residual ethanol and water from the membrane unit to the cooling unit of the dewatering unit for condensing the vaporized permeate stream of vaporized mixture of residual ethanol and water to a liquid permeate stream of residual ethanol and water,
   fifth conduit feeding the liquid permeate stream of residual ethanol and water from the cooling unit into the distillation column for dividing the liquid permeate stream of residual ethanol and water in a distillation step into a second stream of dewatered mixture of ethanol and residual water and into a stream of water, sixth conduit for feeding the second stream of dewatered mixture of ethanol and residual water from the distillation column directly to the evaporator, and seventh conduit for discharging the stream of water from the distillation column.

9. The apparatus according to claim 8, wherein the vapor recompression unit comprises at least one of the following: a mechanical vapor recompression unit and a thermal vapor recompression unit.

10. The apparatus according to claim 8, wherein the recompression unit is configured for feeding continuously a stream of pressurized vaporized mixture of ethanol and water from the vapor recompression unit to the membrane unit.

11. The apparatus according to claim 8, wherein the membrane unit comprises a semipermeable membrane.

12. The apparatus according to claim 8, wherein the membrane unit comprises a porous membrane.

13. The apparatus according to claim 8, wherein the membrane unit comprises a ceramic membrane.

14. The apparatus according to claim 8, wherein the membrane unit comprises a membrane comprising a Zeolite material.

* * * * *

UNITED STATES PATENT AND TRADEMARK OFFICE
CERTIFICATE OF CORRECTION

PATENT NO.        : 8,608,966 B2                                              Page 1 of 1
APPLICATION NO.   : 12/921114
DATED             : December 17, 2013
INVENTOR(S)       : Pasanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this
Twenty-second Day of September, 2015

Michelle K. Lee
*Director of the United States Patent and Trademark Office*